United States Patent [19]

Norel

[11] Patent Number: 4,596,143
[45] Date of Patent: Jun. 24, 1986

[54] METHOD AND APPARATUS FOR DETECTING FRACTURES BY ULTRASONIC ECHOGRAPHY ALONG THE WALL OF A MATERIAL OR A FORMATION

[75] Inventor: Guy Norel, La Celle Saint Cloud, France

[73] Assignee: Institut Francais du Petrole, Malmaison, France

[21] Appl. No.: 565,865

[22] Filed: Dec. 27, 1983

[30] Foreign Application Priority Data

Dec. 27, 1982 [FR] France .................. 82 21831

[51] Int. Cl.$^4$ .................. G01V 1/40; G01N 29/04
[52] U.S. Cl. .................. 73/598; 73/615; 73/629; 73/644; 367/27; 367/35
[58] Field of Search .................. 367/27, 35; 73/588, 73/598, 600, 615, 644, 627, 629

[56] References Cited

U.S. PATENT DOCUMENTS

| | | | |
|---|---|---|---|
| 3,175,639 | 3/1965 | Liben | 367/35 |
| 3,394,586 | 7/1968 | Cross | 73/644 |
| 3,883,841 | 5/1975 | Norel et al. | 73/589 |
| 3,921,442 | 11/1975 | Soloway | 73/644 |
| 4,137,776 | 2/1979 | Rudis et al. | 73/615 |

Primary Examiner—Howard A. Birmiel
Attorney, Agent, or Firm—Antonelli, Terry & Wands

[57] ABSTRACT

A method and apparatus of detecting fractures along the wall of a formation, such as a well formed by test-drilling, provides for the transmission of ultrasonic signals in a direction essentially perpendicular to the wall from a position spaced from the wall by a predetermined distance and the reception of the ultrasonic signals which may be reflected by the wall. The space of predetermined thickness between the transducer which generates the ultrasonic signals and the wall is filled with an intermediate material which does not form a distinct interface with the wall of the type which would be able to produce an appreciable parasitic reflection of the transmitted signals. With this arrangement, if the transducer receives a reflected ultrasonic signal during a time window which begins, following the time of transmission, after a time has elapsed which is essentially equal to the out-and-back travel time of the ultrasonic signals through the space of predetermined thickness, then it will be determined that the wall has no fractures at that point. If no signal is received during the time window, the presence of fractures or small cavities is detected.

8 Claims, 9 Drawing Figures

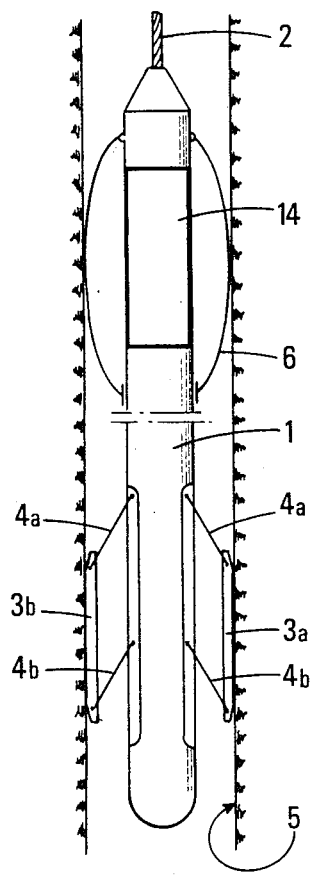
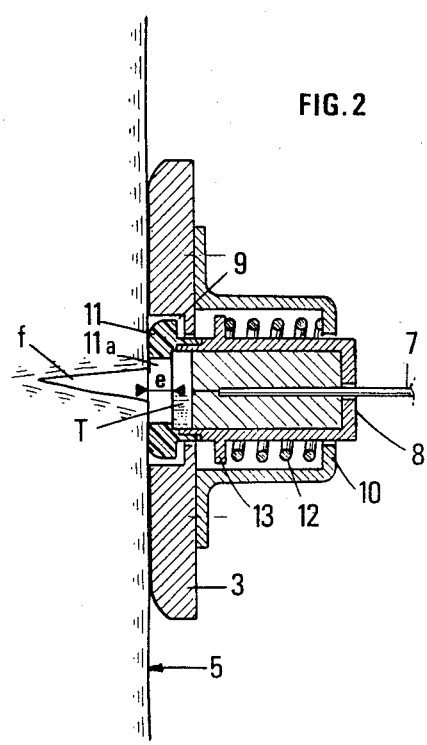

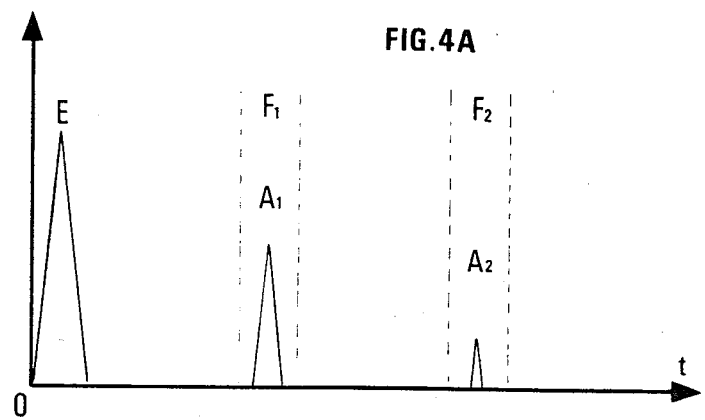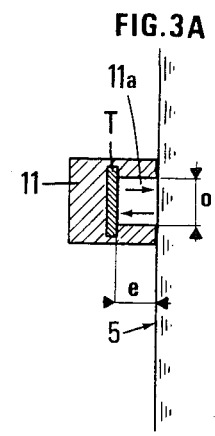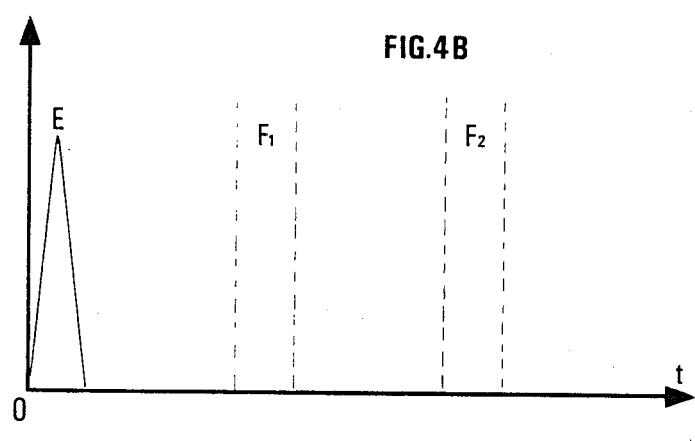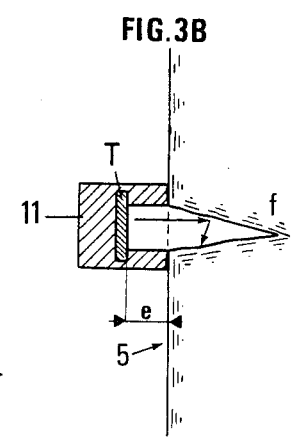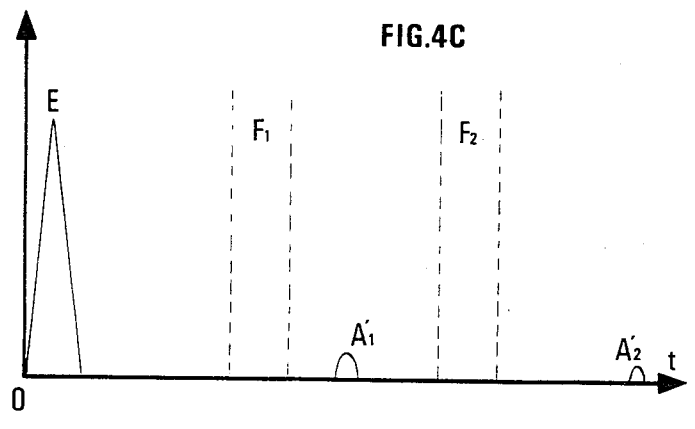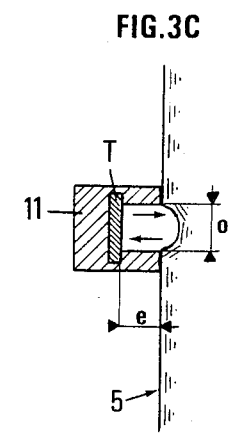

METHOD AND APPARATUS FOR DETECTING FRACTURES BY ULTRASONIC ECHOGRAPHY ALONG THE WALL OF A MATERIAL OR A FORMATION

FIELD OF THE INVENTION

The present invention relates in general to the field of well-logging, and, more particularly, to a method and apparatus for detecting and locating natural or induced fractures along the wall of a material, more specifically, a geological formation which is traversed by a test drilling.

BACKGROUND OF THE INVENTION

The detection of fractures in the wall of a test drilling is currently accomplished using at least one of the following methods: (1) the detection of losses of mud; (2) the interpretation and correlation of porosity measurements, and, in particular, the correlation of porosity measurements provided by low-frequency (20 kHz) sonic logging and neutron logging; (3) the interpretation of anomalies in signals provided by sonic logging or microsonic (300 kHz) logging.

The last of the above-mentioned methods of logging involves transmitting a sonic wave through strata of variable thickness (from 15 to 90 cm), and the variation in the amplitudes of the received signal is dependent not only upon the presence of any fractures, but also on many other parameters, such as porosity, longitudinal and transverse speeds, input and return angles of incidence, intercalations, and the like, in such a way that the interpretation of these types of logging is complex and provides only indirect indications.

British Pat. No. 1,031,200 has already proposed a method by which ultrasonic pulses are sent into a liquid-filled well in a direction which is essentially perpendicular to the axis of the well and the reflected pulses are received along the transmission direction. This patent indicates that the amplitudes and shapes of the reflected waves may provide in particular indications of the existence and locations of cracks in the wall of the well. This patent does not give, however, any precise indication of how these cracks could be detected and describes no means of obtaining sufficient resolution in the detection of the cracks.

U.S. Pat. No. 3,175,639 has also described a well-logging method which also includes the transmission of ultrasonic pulses in a direction which is essentially perpendicular to the axis of a wall and the reception of the reflected ultrasonic pulses along the transmission direction, utilizing an ultrasonic transducer which is applied in direct contact to the cake of mud which covers the wall of the well or which is separated from this case by a known thickness of mud s. The purpose of this method, however, is to determine the porosity and permeability of the geological formation surrounding a test well and concerns itself with the interface between the cake of mud which covers the well wall and the formations which are flooded with water in the vicinity of the well wall. This method, which utilizes a transmission frequency on the order of 10 kHz, is based on determining the acoustic impedance of the water-flooded zone and is in no way suited for precise detection of cracks in the wall of the well.

U.S. Pat. Nos. 3,511,334 and 3,369,626 disclose a logging tool having a rotating component which transmits and receives acoustic signals with a frequency on the order of 1-2 MHz perpendicular to the interface being studied. The reflected signals modulate the intensity of the beam of an oscilloscope, and the absence of a reflected signal in response to a transmitted acoustic signal is interpreted to mean that there is an anomaly in the wall of the well. Such a logging tool has the drawback that in practice it is very sensitive to variations in the diameter of a test drilling because it utilizes a rotating transmitter set which is positioned on the axis of the test drilling, i.e., a transmitter which is spaced relatively far from the wall. The time between transmission and reception thus depends on the variations in the diameter of the test drilling and is affected by mistakes in centering the transmitter-receiver component. In addition, the attachment of this component to a vibrating metal part of the probe body causes significant background noise which disrupts the measurements. Finally, the active surface of the transducer facing the wall of the test drilling is covered by an epoxy resin which creates a break in acoustic impedance and consequently causes multiple echoes upon reception. The existence of this epoxy layer, the acoustic impedance of which is not related to that of the fluid contained in the well (drilling mud), also reduces the acoustic intensity which is transmitted toward the wall of the well.

From French Patent Application No. 2,486,997, there is also known a dip method which utilizes variations in echo amplitudes and correlations of these amplitudes.

Finally, the prior state of the art can be illustrated by U.S. Pat. Nos. 3,356,177 and 4,168,583 which employ a transmitter and receiver which are separated from one another, and U.S. Pat. No. 3,688,569 which employs a component which transmits signals along a direction which is not perpendicular to the surface to be examined.

SUMMARY OF THE INVENTION

The primary object of the present invention is to provide a means of directly revealing fractures with a very fine degree of resolution (on the order of a millimeter), without it being necessary to resort to unreliable correlations with other methods of logging. To do this, at least one transducer (i.e., a transmitter-receiver component) for ultrasonic signals is used which, by creating reflections on the wall of the well, provides a significant reflected signal at a predictable time if the formation is not altered, and no echo at that predictable time or at a predictable level if there is a fracture.

The method of the invention is particularly characterized by the fact that a small aperture angle beam of ultrasonic signals is transmitted and received in the immediate vicinity of the wall through a space of small thickness e, of a known value, in which space there is disposed an intermediate medium which does not form a distinct interface with the above-mentioned wall which would be capable of producing an appreciable parasitic reflection of the transmitted signals. Any reception of ultrasonic signals reflected by the wall is sensitively detected in the direction of transmission during at least a limited interval of time F1, which begins, following the instant of emission, when a time has elapsed which is essentially equal to the out-and-back travel time of the ultrasonic signals through the above-mentioned thickness of the intermediate medium. The reception of signals during the above-mentioned detection interval F1 corresponds to the absence of fractures in the wall of material or the formation, and the absence of reception of signals during the above-mentioned time interval F1 corresponds to the presence of fractures or small cavities in the wall opposite to the transmission point.

The wall is preferably raked or smoothed before the ultrasonic signals are transmitted towards it, especially when the methods of the invention are used to determine the fractures of the wall of a test drilling which traverses geological formations. This raking operation, for example, could be carried out with the aid of a reaming or sweeping tool of a known type, such as a core barrel or a drill bit, and this offers the advantage that it removes from the wall deposits or irregularities which would create recording anomalies other than those caused by the fractures.

The intermediate medium used to fill the space adjacent the ultrasonic signal transducer will be selected in such a way that it provides a low level of attenuation of the acoustic wave. This medium could be, for example, water and/or a solid or liquid, the acoustic impedance of which has essentially the same value as water, such as certain rubbers or polymers (polyethylene, for example), It is known that the acoustic impedance of a material is equal to the product of its specific mass times the speed of propagation of sound in this material. The acoustic wave transmitted could have a frequency of between 400 kHz and 5 MHz.

BRIEF DESCRIPTION OF THE DRAWINGS

These and other objects, features and advantages of the present invention will become more apparent from the following detailed description of preferred embodiments, provided with reference to the accompanying drawings, in which:

FIG. 1 shows a schematic diagram of an ultrasonic probe which employs the method of the present invention;

FIG. 2 shows a cross section of a detection shoe having a built-in transducer in contact with the formation;

FIGS. 3a, 3b and 3c are schematic diagrams which illustrate the method of the invention;

FIGS. 4a, 4b and 4c are signal diagrams which show the various types of signals provided by the probe.

DETAILED DESCRIPTION OF THE PREFERRED EMBODIMENT

Figure 5:
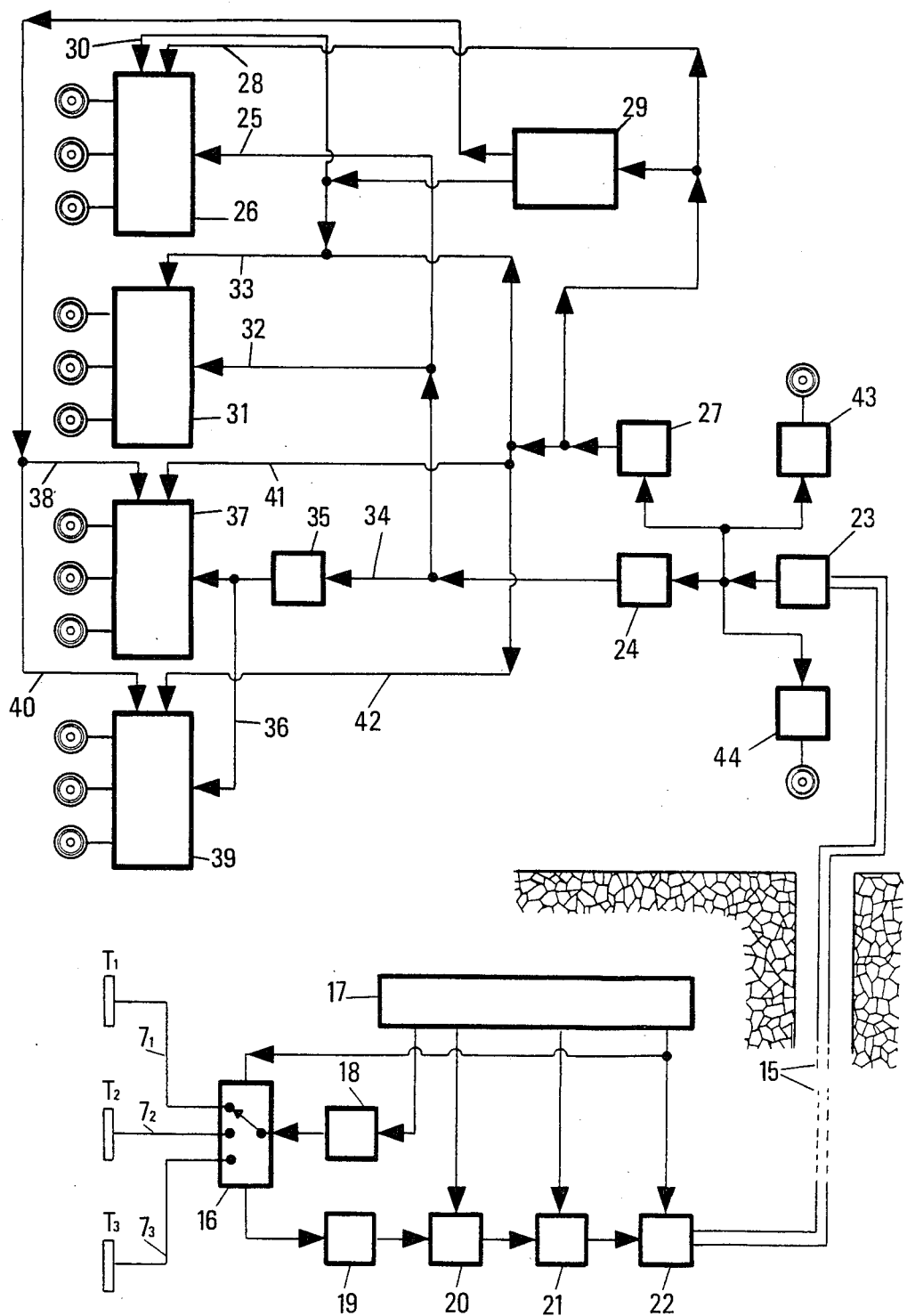
FIG. 5 is a schematic block diagram of the transmission, reception and signal processing circuits.

In FIG. 1, a tool body or probe body 1 is suspended at the end of a cable 2. Electrical conductors which transmit to the probe the energy required for its operation and which, on the surface, transmit the signals delivered by the probe may be incorporated into this cable 2.

Probe body 1, for example, may be equipped with four measurement shoes which are arranged in diametrically-opposing positions in pairs and placed so as to be positioned against the wall. Only two of these shoes are shown at 3a and 3b in FIG. 1. They are connected to the probe body 1 by a mechanism, not shown in detail, which includes articulated arms 4a and 4b for moving the shoes with respect to the axis of the probe body 1 and for placing them in contact with wall 5 of the well during the measurements. Probe body 1 is also equipped with a centering device 6 of generally-known construction.

As FIG. 2 shows, each shoe 3 comprises an acoustic wave transmitter-receiver transducer T of the piezoelectric type which, when an electrical signal transmitted by conductor 7 is received, emits an acoustic pulse, and which, when an acoustic pulse is received, delivers an electric signal to be transmitted by conductor 7. The transmission and reception pattern of transducer T is selected to be highly directive. In addition, this transducer is placed in the immediate vicinity of the wall, and it emits a heavily-directional beam in a direction which is essentially perpendicular to the axis of the probe and receives the acoustic waves which are reflected perpendicularly to the axis of the probe.

Transducer T is mounted in a housing 8 which is placed in a bore of measurement shoe 3. This bore opens towards wall 5 of the well and housing 8 is mounted in such a way that it slides in a cover-shaped element 10 which is attached to the other face of shoe 3 opposite the wall 5.

Housing 8 is biased by spring 12 against the wall 5 of the test drilling. The contact with this wall 5 is made by a ring 11, which is preferably made of plastic, of a selected thickness e, so that the travel time of the trains of acoustic waves through recess 11a, which is filled with water or a material which has essentially the same acoustic impedance and which constitutes an intermediate medium between transducer T and wall 5, is well known. Spring 12, which is placed between the bottom of receptacle 9 and a shoulder 13 of housing 8, keeps ring 11 in contact with wall 5 of the well by moving the housing 8 in a direction perpendicular to the axis of the probe.

The resolution obtained will be better the smaller the diameter or aperture 0 of the collimator which is represented by recess 11a. This aperture will, however, be sufficient to prevent the diaphragm from significantly attenuating the emitted acoustic beam. On the other hand, it is known that the aperture angle of the acoustic wave beam emitted decreases when the transmission frequency is increased. The value of the thickness e is taken into account in order to determine the positions of the time windows or limited intervals of detection time F1 and F2 in which the successive echoes A1, A2, ... of the emitted ultrasonic signal E are detected. FIGS. 3a, 3b and 3c, where time t appears on the abscissa, show different examples of the detection response to material surfaces of different configuration. These windows F1 and F2 correspond to the times when the successive reflections of signal E at the interface between wall 5 and the water contained in recess 11a are received.

The thickness e defines the mean distance between transmission element T and wall 5. This thickness will be selected to be sufficient to allow window F1 to be shifted enough from the transmission time to ensure good separation between signal A1 and transmitted signal E (FIG. 4a) while thickness e, however, is limited in order to avoid excessive attenuation of the acoustic signals by the intermediate medium with allowance for the value of the acoustic transducer's transmission power. Excellent results are obtained in practice with values of e ranging from several millimeters to 1 cm, but these values should not be considered limiting.

The probe 1 is also equipped with a diameter determining device (not shown) which indicates the value of the diameter of the bore hole at the level where ring 11, which plays the role of tracer, makes contact with the inner wall 5 of the test drilling. Such a device, which is well known from the prior art, does not need to be described in detail. For example, this device indicates the value of the diameter of the hole with allowance for the rotation of articulated arms 4a and 4b and can in particular be used to detect the presence of significant cavities in the wall of the test drilling.

The detection of fractures f is carried out with ultrasonic waves which are likely to reflect well and are not excessively attenuated by traversing the plug of water, or more generally, the intermediate element of thickness e. Excellent results are obtained by using acoustic waves which have a frequency of between 400 kHz and 5 MHz, and the thickness e of the plug 11a of water can be selected, depending on the value of this frequency, to be between 1 mm and several centimeters. The attenuation of the signal transmitted obviously increases with the frequency selected.

With the probe placed in a given position at a known level of the test drilling, the transducer transmits through the intermediate element plug 11a a signal which echoes and returns to the transducer if the formation is compact (FIG. 3a) and which is not returned if the zone is fractured (FIG. 3b). In the first case, the transmitted signal E returns in echoes A1 and A2 such that 0A1=A1A2=out-and-back time in the plug of water.

If the wall of the test drilling has small cavities, there may be echoes A'1, A'2, . . . , beyond window F1 (FIG. 3c). However, one of these echoes may possibly appear in window F2. This second time window F2 is not essential, but its use has the advantage of supplementing the indications given by time window F1, and the following cases may thus arise: (1) no echo in F1: there is a fracture; (2) echo in F1: there is no fracture, as confirmed by the presence of another echo in time window F2; (3) no echo in F1 but an echo beyond this time window, including F2, indicating that there is an alveolus at the level under consideration.

FIGS. 4a, 4b and 4c show the signals corresponding to these different cases which are produced on the screen of an oscilloscope or on a recording. The locations of the fractures will be obtained either by measuring at a fixed level of the test drilling or by slowly moving the probe along the wall of the test drilling. In the selected time window F1 or F2, the return signal obtained is integrated as a function of the measurement reading with a time constant which decreases in size the more the operator wishes to increase the resolution of the measurement, and the thickness of the fractures can vary from several dozens of microns (cracks) to several millimeters.

When the invention is employed, use will be made of at least time window F1 which defines a limited time interval which begins, following the instant of transmission of signal E, when a time has elapsed which is essentially equal to the out-and-back travel time of the ultrasonic signals through thickness e of the intermediate medium which separates transducer T from wall 5.

The interpretation of the logs obtained is improved, as indicated above, by detecting the reception of any ultrasonic signals reflected during at least an additional limited time interval, or time window, such as F2, which begins, following the instant of transmission, when a time has elapsed which is essentially equal to twice, or more generally, a multiple of the out-and-back travel time of the ultrasonic signals to the above-mentioned thickness e, of a known value, of the intermediate medium.

In FIG. 5 which shows schematically the transmission, reception and signal processing circuits, the bottom of the drawing shows the acoustic signal transmission and reception circuits located within probe 1, while the top of the figure shows the circuits for processing the electrical signals. These processing circuits are preferably located on the surface of the ground and are connected to the circuits within the probe by electrical transmission conductors 15, which can be incorporated into cable 2 which supports the probe.

By way of example, it was assumed that the probe includes three transducers T1, T2 and T3 which may (or may not) be distributed in the same horizontal plane around the probe (for instance, spaced at intervals of 120° in this plane).

An electric switching circuit or multiplexer 16, which is electrically connected to the three transducers by conductors according to FIG. 5, respectively, and which is powered by a low-frequency current (40 Hz, for example) from a timing control circuit 17, connects in succession transducers T1, T2 and T3 to a signal transmitter circuit 18 which controls the ultrasonic transmission from the transducers T1, T2 and T3. This circuit 18 is powered by a high-frequency current (10 kHz, for example) from timing control circuit 17.

Switching circuit 16 is also connected to a signal receiver circuit 19, which receives the electrical signals generated by the transducers T1, T2 and T3 when acoustic echoes corresponding to the emitted ultrasonic signals E are received. The electrical signals at the output of signal receiver circuit 19 are applied to an amplifier circuit 20 with a programmable gain, which also filters these signals. The circuit 20 is coordinated with the frequency of transducer T, for example, with a frequency on the order of 2.5 MHz, and is powered by timing control circuit 17 with a current having a frequency of 10 kHz.

The output from amplifier circuit 20 is applied to a sampler-rectifier circuit 21 and, from there, to an output amplifier 22, which is connected to electrical conductors 15 for transmission to the surface of the electrical synchronization signals generated by timing control circuit 17 as well as electrical signals corresponding to the transmission and reception of acoustic signals by transducers T1, T2 and T3.

The electrical signals received on the surface are applied to the input of an amplifier 23, the output of which is connected to a first threshold circuit 24, which is connected by a conductor 25 to a mean value detector circuit 26 which determines the mean value of the signal received in the time interval corresponding to time window F1 for each of the three transducers T1, T2 and T3, respectively. The circuits for determining time windows F1 and F2 comprise a synchronization circuit 27, the input of which is connected to the output of amplifier 23 and the output of which is connected, on the one hand, to circuit 26 by way of conductor 28 and, on the other, to the input of a timing circuit 29 for generating time windows F1 and F2. The output of this timing circuit 29 is connected to circuit 26 by way of conductor 30.

When they leave the first threshold circuit 24, the signals are also applied to an oscilloscope 31 via conductor 32. Oscilloscope 31 is connected by conductor 33 to timing circuit 29, which defines time window F1, and to the synchronization circuit 27. The signals leaving first threshold circuit 24 are also applied via conductor 34 to a second threshold circuit 35, the output signals of which are applied to an oscilloscope 37 which is connected by conductor 38 to timing circuit 29 which defines time window F2. The output signals of second threshold circuit 35 are also applied via conductor 36 to a mean value detector circuit 39 which determines the mean value of the signal received in the time interval corresponding to window F2 for each of transducers T1, T2 and T3, respectively. This circuit 39 is connected by conductor 40 to circuit 29 which defines time window F2. Conductors 41 and 42 connect oscilloscope 37 and circuit 39, respectively, to synchronization circuit 27.

Threshold circuits 24 and 35 will be adjusted in such a way as to eliminate parasitic echoes, between element T and wall 5, due to the use of materials which have an acoustic impedance which is not rigorously adapted to that of the water in contact with wall 5. The synchronization circuit 27 detects the synchronization signals provided by the timing control circuit 17 and appearing at the output of amplifier 23 so as to synchronize the operations of the mean value detector circuits 27 and 39, the oscilloscopes 31 and 37, and the timing circuit 29 to the multiplexing of data signals from transducers T1, T2 and T3 by the switching circuit 16.

The output of amplifier 23 is also connected to an amplifier 43, which makes it possible to record signals on magnetic tape, and to an amplifier 44 which makes it possible to read the magnetic recordings which are thus made.

Of course, the apparatus includes means for determining the position of the probe in the well during each measurement. This will make it possible to record the measurements made as a function of depth. These means can be of the type currently used for known well-logging probes.

It may also be possible to use a membrane to close recess 11a which contains the water or another intermediate medium which has essentially the same acoustic impedance and attenuates the acoustic waves only slightly, provided that this thin membrane is composed of a material which has acoustic characteristics such that this membrane does not introduce into windows F1, F2, . . . , appreciable parasitic reflections of the signals which are transmitted and reflected by the wall of the formation (a membrane made of a material which has essentially the same acoustic impedance as water, such as polyethylene).

Recess 11a can also be filled with a solid which has essentially the same acoustic impedance as water.

While I have shown and described several embodiments in accordance with the present invention, it is understood that the same is not limited thereto but is susceptible of numerous changes and modifications as known to a person skilled in the art, and I therefore do not wish to be limited to the details shown and described herein, but intend to cover all such changes and modifications as are obvious to one of ordinary skill in the art.

What is claimed is:

1. Method of detecting fractures along the wall of a material, such as a geological formation, in which ultrasonic signals are transmitted along a direction which is essentially perpendicular to said wall from at least one transmission element, spaced from the wall, through an intermediate medium, and the reflected signals are received in this same direction, comprising the steps of transmitting and receiving a narrow-aperature-angle beam of ultrasonic signals in the immediate vicinity of the wall through a space of small thickness of a known value in which there is disposed an intermediate medium consisting of a material which forms no interface distinct from that of said wall which would be able to produce any other appreciable reflection of the transmitted signals than that produced by said wall; and establishing a state of reception of ultrasonic signals reflected by the wall essentially along the transmission direction during at least one limited time interval which begins, following the time of transmission, when a period of time has elapsed which is essentially equal to the out-and-back travel time of the ultrasonic signals through said thickness of known value of the intermediate medium; and determining from the absence of reception of signals during said limited time interval the presence of fractures or small cavities in the wall opposite the point of transmission; and wherein the reception of any ultrasonic signals reflected is detected during at least a supplementary limited time interval which begins, following the instant of transmission, when a time has elapsed which is essentially equal to a multiple of the out-and-back travel time of the ultrasonic signals through the above-mentioned thickness of a known value of the intermediate medium.

2. Method of claim 1, wherein smoothing of the wall is carried out before the ultrasonic signals are transmitted towards it.

3. Method of claim 1, wherein said intermediate medium is water.

4. Method of claim 3, wherein a membrane which has essentially the same acoustic impedance as water forms a wall of said space of known thickness adjacent the wall of the material.

5. Method of claim 1, wherein an acoustic wave having a frequency of between 400 kHz and 5 MHz is transmitted.

6. Apparatus for detecting fractures along the wall of a material, such as a geological formation to be studied, comprising transducer means for transmitting a small aperture angle beam of ultrasonic signals and for generating output signals upon receiving a reflection of those ultrasonic signals from said wall, means for supporting said transducer means adjacent said wall so that said ultrasonic signals are transmitted in a direction which is essentially perpendicular to said wall and said transducer is spaced from said wall by a predetermined distance, including means defining a space between said transducer means and said wall which has a thickness equal to said predetermined distance and which space contains an intermediate medium consisting of a material which forms no interface distinct from that of said wall which would be able to produce any other appreciable reflection of the transmitted signals than that produced by said wall; and means connected to said transducer means for detecting the absence of output signals generated thereby during a limited time interval which begins, following the time of transmission of said ultrasonic signal, when a period of time has elapsed which is essentially equal to the out-and-back travel time of the ultrasonic signals through said space containing said intermediate medium, as an indication of the presence of fractures or small cavities in the wall opposite the point of transmission, including means for detecting any output signals generated by said transducer means during a secondary limited time interval subsequent to said first-mentioned limited time interval and which begins, following the time of transmission of said ultrasonic signal, when a period of time has elapsed which is essentially equal to a multiple of the out-and-back travel time of the ultrasonic signals through said space containing said intermediate medium.

7. Apparatus of claim 6, wherein said intermediate medium is water.

8. Apparatus of claim 6, wherein said means defining said space between said transducer means and said wall includes a membrane having the same acoustic impedance as said intermediate medium for bounding said space opposite said transducer means, and a ring surrounding said space between said membrane and said transducer means.

* * * * *